United States Patent
Prodinger et al.

(10) Patent No.: US 6,291,239 B1
(45) Date of Patent: Sep. 18, 2001

(54) MONOCLONAL ANTIBODY

(76) Inventors: Wolfgang Prodinger, Kirschentalgasse 16, A-6020 Innsbruck; Michael Schwendinger, Semmelweisgasse 4, A-7100 Neusiedl/See, both of (AT)

(*) Notice: Subject to any disclaimer, the term of this patent is extended or adjusted under 35 U.S.C. 154(b) by 0 days.

(21) Appl. No.: 09/276,296

(22) Filed: Mar. 25, 1999

(51) Int. Cl.[7] .................. C12N 5/06; C12Q 1/70; G01N 33/53; C07K 16/00; A61K 39/395

(52) U.S. Cl. .................. 435/339.1; 435/5; 435/7.1; 435/334; 530/388.1; 530/388.35; 424/141.1; 424/143.1; 424/159.1

(58) Field of Search .................. 435/5, 7.1, 334, 435/339.1; 530/388.1, 388.35; 424/141.1, 143.1, 159.1

(56) References Cited

FOREIGN PATENT DOCUMENTS

WO 96/17625  6/1996 (WO) .................. A61K/47/48

OTHER PUBLICATIONS

Molecular Immunology, vol. 35, No. 6–7, Apr. 1998, p. 392, XP–002089603, "Characterization of C3DG Binding to a Recess Formed Between SCR 1 and SCR 2 of Complement Receptor Type Two", Prodinger.

Immunopharmacology, vol. 38, No. 1–2, Dec., 1997, pp. 141–148, XP002089604, "Expression in Insect Cells of the Functional Domain of CD21 (Complement Receptor Type Two) as a Truncated. . ", Prodinger.

Journal of Immunology, vol. 156, No. 7 Apr. 1, 1996, pp. 2580–2584, XP002089605, "Ligation of the Functional Domain of Complement Receptor Type 2 (CR2, CD21) is Relevant for Complex . . . ", Prodinger.

Journal of Immunology, vol. 154, No. 10, May 15, 1995, pp. 5426–5435, XP002089606, "Characterization of a Complement Receptor 2 (CR2, CD21) Ligand Binding Site for C3", H. Molina et al.

Journal of Immunology, vol. 161, Nov. 1, 1998, pp. 4604–4610, XP002089607, "Characterization of C3dg Binding to a Recess Formed Between Short Consensus Repeats 1 and 2 . . ", Prodinger.

Primary Examiner—Hankyel T. Park
(74) Attorney, Agent, or Firm—Lorusso & Loud

(57) ABSTRACT

A monoclonal antibody (FE8) against human complement receptor type 2 CR2, CD21) which is able to substantially remove C3-derived fragments already attached to CR2, in particular C3dg from CR2 at temperatures of 25° C. and above. Furthermore, the invention covers hybridoma cells and processes to obtain antibodies, as well as therapeutic applications.

23 Claims, 7 Drawing Sheets

FLUORESCENCE

FLUORESCENCE

NO FLUORESCENCE

NO FLUORESCENCE

MONOCLONAL ANTIBODY

BACKGROUND OF THE INVENTION

1. Field of the Invention

The invention relates to a monoclonal antibody (mAb) against human complement receptor type 2 (CR2, CD21) and a hybridoma as well as process to obtain the same. Furthermore, the invention is directed to therapeutic applications thereof.

2. Description of the Related Arts

Human CR2 (CD21) is a membrane glycoprotein of 145 kDa predominantly expressed on mature B lymphocytes (Tedder, T. F., L. T. Clement, and M. D. Cooper. 1984. Expression of C3 d receptors during human B cell differentiation: immunofluorescence analysis with the HB5 monoclonal antibody. *J. Immunol.* 133:678) and follicular dendritic cells (Reynes, M., J. P. Aubert, J. H. Cohen, J. Audouin, V. Tricottet, J. Diebold, and M. D. Kazatchkine. 1985. Human follicular dendritic cells express CR1, CR2, and CR3 complement receptor antigens. *J. Immunol.* 135:2687), and to a much lesser extent on peripheral blood T lymphocytes, thymocytes or astrocytes. The function of CR2 has been most extensively studied for B-lymphocytes (for a review, see Fearon, D. T. and R. H. Carter. 1995. The CD19/CR2/TAPA-1 complex of B lymphocytes: Linking natural to acquired immunity. *Annu. Rev. Immunol.* 13:127). CR2 is the receptor for special CR2-binding fragments, in particular for C3dg and (with lower affinity) for iC3b, fragments of C3 that are generated during complement activation and covalently deposited on surfaces e.g. of pathogens. On B-cells, CR2 forms a non-covalent receptor complex with the B-cell specific CD19 molecule and CD81 which is broadly expressed among hematopoietic cells. Coligation of this complex and the BCR-complex lowers the threshold for B-cell activation substantially. The extent of this effect is exponentially correlated to the number of C3dg-residues on the specific antigen.

Of pathophysiological relevance, Epstein-Barr virus infection of human cells is known to require attachment to CR2 as a first step.

CR2 is a member of the family of C3b-binding and/or C4b-binding proteins and its extracellular part is formed by 15 or, as a result of alternative splicing, 16 short consensus repeats (SCR). These structural units of about 60 amino acids share a frame of several strictly conserved amino acids, most importantly four cysteine residues which are linked by disulfide bonds in a way that the first and third Cys and the second and fourth Cys form a bond, respectively.

Characterization of the two N-terminal SCRs involved in ligand binding has extensively made use of the mouse mAb OKB7 which was shown early to inhibit CR2-dependent EAC3d-rosetting of Raji cells (Rao, P. E., S. D. Wright, E. F. Westberg, and G. Goldstein. 1985. OKB7, a monoclonal antibody that reacts at or near the C3d binding site of human CR2. *Cell. Immunol.* 93:549) and to reduce infection of B-cells with EBV (Nemerow, G. R., R. Wolfert, M. E. McNaughton, and N. R. Cooper. 1985. Identification and characterization of the Epstein-Barr virus receptor on human B lymphocytes and its relationship to the C3d complement receptor (CR2). *J. Virol.* 55:347). OKB7 has also been employed to demonstrate an epitope dependence regarding effects of CR2-mAbs on B-cell proliferation. However, this feature of OKB7 versus other non-blocking mAbs as HB5 (Tedder, T. F., L. T. Clement, and M. D. Cooper. 1984. Expression of C3d receptors during human B cell differentiation: immunofluorescence analysis with the HB5 monoclonal antibody. *J. Immunol.* 133:678) is not consistently defined.

Although mAb OKB7 inhibited EAC3d-rosetting with CR2-expressing cells to >95% in our hands, it was rather inefficient in blocking CR2-dependent complement activation on Raji cells. It is, therefore, an object of the invention to generate more effective mAbs. Further objects are the generation of corresponding hybridomas and therapeutic applications. To this end, employing a baculovirus-derived soluble CR2-protein truncated after SCR 4 (Prodinger, W. M., J. Schoch, M. G. Schwendinger, J. Hellwage, W. Parson, P. F. Zipfel, and M. P. Dierich. 1997. Expression in insect cells of the functional domain of CD21 (complement receptor type two) as a truncated soluble molecule using a baculovirus vector. *Immunopharmacology* 38:141) as an immunogen and inhibition and removal of the binding of FITC-labelled, C3d-coated agarose microbeads to CR2 as a screening method proved to be a successful strategy.

BRIEF SUMMARY OF THE INVENTION

This and other objects are solved by a monoclonal antibody (FE8) against human complement receptor type 2 (CR2, CD21) which is able to substantially remove C3-derived fragments already attached to CR2, in particular C3dg from CR2 at temperatures of 25° C. and above. The term "substantially removes" means that C3-derived fragments (such as polymeric C3dg) are removed from fully loaded CR2 to an extent of at least 70%, preferably at least 90%. Such a mAb has beneficial properties discussed below. It is essential that the mAb (called FE8) according to the invention is not only able to block C3dg from binding to CR2 but is able to substantially remove C3dg from CR2. This has not been the case for prior art mAb OKB7. Such potential is also not disclosed in EP 358 130 (Götze).

A process to obtain such antibodies (or hybridoma cells producing such antibodies) is characterised by the steps:

a) Preparing a CR2 molecule comprising at least short consensus repeats SCRs 1 to 2 of CR2, and preferably SCRs 1 to 4 of CR2.

b) Immunising rodents, in particular mice, with a solution thereof, which is preferably made in PBS at pH 8.5, c) Fusing spleen cells from these rodents with a myeloma cell line and culturing these fused cells, preferably with HAT medium, d) Preparing carrier particles, coating them with a C3-derived fragment binding to CR2, in particular with C3d, and labeling them with tracers, preferably fluoresceinisothiocyanate (FITC), e) Selecting hybridoma clones which produce monoclonal antibodies by testing, preferably by fluorescence activated cell sorting, their cell culture supernatants for the potential to remove from CR2 said coated carrier particles after they had bound to CR2-expressing cells.

Steps a) to c) are essentially prior art. However, so far it is new to use SCRs 1 up to 4. The technique of step d) is essentially known per se from an earlier publication, i. e. Prodinger, W. M., C. Larcher, M. Schwendinger, and M. P. Dierich. 1996. Ligation of the functional domain of complement receptor type 2 ( CR2, CD21) is relevant for complex formation in T cell lines. *J. Immunol.* 156:2580, but has never been used in the present context. Step e) leads to hybridoma clones (producing antibodies) with the desired properties.

DETAILED DESCRIPTION OF THE INVENTION

Figure 1:
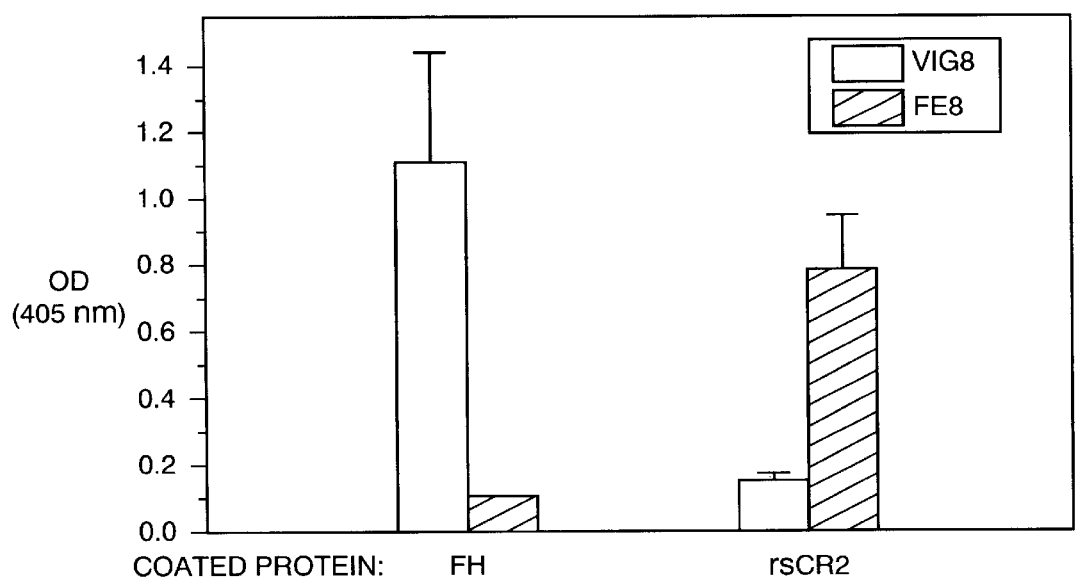
FIG. 1 graphically demonstrates that FE8 bound to rsCR2, but not to structurally similar FH.

According to a preferred embodiment of the invention, monoclonal antibodies with the specificity of FE8 can be obtained by the use of a soluble recombinant form of CR2 comprising SCRs 1 through 4 (named rsCR2.1–4) expressed in Spodoptera frugiperda insect cells (Sf9 cells). Accordingly, this rsCR2.1–4 can be used for immunisation of mice subcutaneously at a dosage of 10 µg in 50 µl sodium-phosphate buffered physiologic saline solution (PBS) mixed with equal amounts of complete Freund's adjuvant. Booster immunisations are done with the same amount of rsCR2.1–4 and incomplete Freund's adjuvant according to standard prodecures and finally with 100 µg rsCR2.1–4 in PBS injected intraperitoneally. Three days thereafter the immunised animals are sacrificed and fusion of spleen cells with the myeloma cell line P3X63Ag8.653 is performed by standard procedures first described by K öKohler and Milstein and later modified by Galfre and coworkers.

Furthermore, the next step is selective culturing of hybridoma clones in hypoxanthin-aminopterin-thymidine medium and screening hybridoma supernatants for removing the CR2-C3dg interaction. To this end, agarose beads of a diameter of less then 1 µm are prepared, multiply coated with C3dg and labeled with a fluorescent dye, for example fluoresceinisothiocyanate (FITC) as essentially described by W. M. Prodinger and coworkers (*J.Immunol.*, 1996, 156:2580–2584) to form C3dg-FITC-beads. Screening for monoclonal antibodies which remove or dissociate CR2-C3dg interaction is performed by testing the adherence of an optimal amount of C3dg-FITC-beads to one million of Raji B-lymphoblastoid cells in a culture volume of 60 µl at room temperature or above. Hybridoma cells which produce an antibody able to reduce beads attachment to background levels at a concentration well below 10 µg/ml can be selected for further subcloning and generation of monoclonal Ig by standard methods.

Such hybridoma cells have been e.g. deposited at ECACC (European Collection of Cell Cultures, Salisbury, Wiltshire, SP40SG, UK) under No. 98072910 on Jul. 29, 1998.

In particular in view of pathophysiological relevance it is preferable to have a mAb which is able to dissociate a C3-derived fragment (C3dg) which is bound to the aminoterminal short consensus repeats SCRs 1 and 2 of CR2.

The dissociating or removing properties are preferably present at low mAb concentrations as 0.3 µg/ml.

Another aspect of the invention is a mAb against human complement receptor type 2 (CR2), the mAb recognizing a discontinuous epitope on the aminoterminal short consensus repeats SCRs 1 and 2 of CR2. Preferably the mAb most intensively reacts with a CR2 epitope located between said SCR1 and SCR2 units, wherein CR2 epitope between SCR1 and SCR2 has the amino acid sequence EYFNKYSS (as designated by single letter code).

FE8 recognizes a discontinuous epitope. In order to define the amino acid residues contributing to this epitope, a library of 126 hexapeptides overlapping by 5 residues covering the sequence of SCR 1 and SCR 2 (i. e., 131 amino acids) was synthesized and assayed for binding of FE8 by the peptide scanning technique. Several spots were clearly recognized. Peptides 63 and 64 (EYFNKY and YFNKYS) reacted most intensively. Together with the weaker stained peptide 65 (FNKYSS) they comprise the eight amino acids between the fourth Cys of SCR 1 and the first Cys of SCR 2 and thus the entire link region between SCRs 1 and 2. Incorporation of either of the neighbouring cysteines C62 and C71 abrogated antibody binding. The third intensively stained spot was observed with peptide 16 (YYSTPI) which directly follows the sequence 8-PILNGRIS-15 that has been described by others as important for binding of OKB7 and iC3b. Peptides 8 and 9 which span that sequence were not stained, peptide 11 (NGRISY) reacted faintly. A weak reaction was also observed with peptides 87, 88 and 105. Peptide 105 is directly followed in sequence by peptides 110/111 which reacted more clearly.

The inventive mAb preferably belong to the mouse immunoglobulin subclass lgG1, κ.

Apart from the properties set forth above, the mAb according the invention is able to inhibit completely infection of (human) CR2 expressing cells with the Epstein-Barr virus (EBV), preferably already at a concentration of 0.1 µg/ml (and 8×10$^5$-tonsillar B-cells per ml).

The monoclonal antibodies according to the invention also have therapeutic applications:

OVERVIEW

The human immune system has two effector mechanisms which are intricately connected with each other: (A) the specific immune system with B and T lymphocytes, the cells which generate antigen-specific antibodies and killer-cells and (B) the innate (or unspecific) immune system consisting of soluble effector molecules like those of the complement system or like interferons or lysozyme, and consisting furthermore of antigen-nonspecific phagocytic cells and natural killer cells. In general, substances foreign to the organism are recognised by both branches of the immune system, marked as such, destroyed and prohibited to cause damage in the body again. Antigens belonging to the body itself (self tissues), however, are not attacked by the immune system under normal conditions, but instead induce immunological tolerance.

The complement system is the main humoral, i.e. plasma-protein based, system of innate immunity. Complement influences both unspecific phagocytic cell activity and generation of specific antibodies. The central protein of the complement system is C3. When C3 is activated, e.g. by pathogens, it changes into biologically active C3b. C3b forms a covalent bond with nearby molecules, e.g. surface proteins of the pathogen. By contact with other plasma proteins, C3b is inactivated into C3dg which, as a remnant of complement activation, tags foreign particles as "foreign". As such, C3dg interacts specifically with CR2 on cells of the immune system.

The CR2 protein is structured into extracellular "short consensus repeats" (SCRs) of which only SCRs 1 and 2 are important for binding of C3dg. The same part of CR2 is the site of attachment of the Epstein-Barr virus, a worldwide prevalent herpesvirus.

CR2 is found in particular on B lymphocytes (B-cells) which effect the specific antibody response, and on follicular dendritic cells (FDC). On B-cells, C3dg-CR2 interaction induces faster multiplication of the cell and further specialisation towards antibody production. CR2 on FDC is primarily a molecule for retaining C3dg-coated antigens on the surface, but effects on the FDC itself and transmitted through CR2 have not been described in detail so far.

Both cell types also interact with each other through C3dg-coated antigen. This interaction is critical for the affinity and longevity of the antibody response to the antigen. Binding of B-cells to FDC via the C3dg-antigen trapped on the FDC-surface allows them to improve the antibody molecule that is produced and, in parallel, to generate memory cell offspring which preserves the production of this antibody for years.

In certain autoimmune diseases (for example Myasthenia gravis or Thrombocytopenia) abnormal immune responses take place which are caused by production of antibodies acting against self tissues. In the above diseases these are the structures transmitting the signals from nerves to muscles or the platelets which are important for blood clotting, respectively. They are treated with immunosuppressive agents of different chemical background and mode of action, all of which present with severe side-effects. Therefore, interference with the pathological process within the lymphatic system that causes autoantibody production may be a better targeted therapeutic approach.

In this respect it is beneficial that the monoclonal antibody FE8 interferes with delivery of C3dg-coated antigens to FDC and the trapping of antigen and its presentation by FDC. This is stressed by the fact that pathogenic autoantibodies (as present in the above diseases) are predominantly of high affinity and of the IgG isotype. This means that they derive from B-cells which have interacted with FDC to undergo this "improvement" of their antibody product. Therefore, the monoclonal antibody FE8 may be useful for therapy of autoantibody-associated diseases.

By occupational accidents such as the inadvertent parenteral application of complete Freund's adjuvant (CFA) an immune response against self tissue can be initiated in a healthy person. The inflammation at the CFA-damaged site causes tissue destruction and complement activation. Generation of C3dg, either soluble C3dg or C3dg coated to deformed self tissue can be crucial in the emerging autoimmune response. From experiments with genetically engineered mice two modes of action can be envisaged: either soluble C3dg allows otherwise inhibited autoantibody-producing cells to overcome the inhibitory threshold, or C3dg-tagged self tissue remnants become autoimmunogenic and stimulate B-cells.

In both cases the effect would be transmitted via CR2, and abrogation or inhibition of its interaction with C3dg can be seen as a therapeutic intervention.

As mentioned above, CR2 comes into direct contact with the Epstein-Barr virus (EBV) which uses CR2 as the port of entry into human B-cells. EBV establishes a lifelong persisting infection. More than 90 percent of adults are infected with EBV. Mostly this is not associated with apparent disease. Upon primary infection, only some individuals develop a self-limiting benign disease, infectious mononucleosis. However, EBV can contribute to the development of malignant or benign tumours. It is implicated in Burkitt's lymphoma, a Non-Hodgkin lymphoma of high malignancy mostly affecting children in tropical climates. Furthermore, EBV seems to play a role in development of nasopharyngeal carcinoma, a lymphoepithelial tumour frequently seen in China. EBV can also cause B-cell lymphoma development in individuals immunosuppressed by infection with HIV. All these proliferative diseases are difficult to treat and mostly require severe cytostatic therapy and/or irradiation. EBV also causes severe complications in patients undergoing transplantation of solid organs or bone marrow. Under circumstances when intensive immunosuppressive therapy is required, e.g. to stop graft rejection, EBV can induce the potentially life-threatening B lymphoproli-ferative syndrome. This disease can be either self-limited or very difficult to treat. Some success was achieved with a combination of monoclonal antibodies against CR2 and CD24, although the anti-CR2 antibody was not able to block EBV-binding to CR2.

It can be imagined that this disease can be more successfully treated using a monoclonal antibody that also blocks EBV attachment to cells. Furthermore, FE8 or a "humanised" derivative (having lost its mouse-protein character) may be used in a prophylactic approach in individuals which are at risk to develop such diseases.

In general it should be noted that for the purpose of this invention, monoclonal antibody means the monoclonal antibody itself, but also a CR2-binding fragment thereof or a recombinant construct comprising the variable domains (Fv) of the mAb either alone or in combination with other amino acid sequences, preferably derived from other immunoglobulin molecules.

C3dg-coated antigens presented on FDC need not only be breakdown products of pathogens. Smaller pathogens like viruses can become coated with complement without being destroyed by this process, but instead being trapped as infectious particles on the FDC surface. For example, HIV coated with complement has been demonstrated to become trapped on FDC of lymph nodes. This occurs notably also in very early stages of infection: in experiments where monkeys were inoculated with SIV (the simian counterpart of HIV), administered virus is soon found predominantly bound on lymph node FDC. As FDC—in contrast to other antigen-presenting cells—do not degrade trapped antigen, but present it unmodified, HIV trapped in this way on FDC retains its infectivity over a long period of time. This means that FDC can function as a reservoir of infectious HIV in lymphatic organs, where it is constantly accessible for T lymphocytes, the prime target cells for HIV.

The monoclonal antibody FE8 is shown to be effective in displacement of complement-coated HIV from commonly used CR2-positive Raji B-cells. This demonstrates that the virus can be displaced from cells by interference with CR2. Furthermore, the monoclonal antibody FE8 was also demonstrated to block binding (and dissociate) C3dg-carrying particles from FDC. Therefore, FE8 may reduce the amount of C3dg-coated virus bound to FDC. This would be helpful in treatment of HIV-infection as the amount of virus in the vicinity of T cells, the targets of HIV, is reduced. A reduction of FDC-trapped HIV may already be effective immediately after exposure to the virus, e.g. after a needle-stick injury with HIV positive blood, or at later stages of HIV-infection. Due to the novel approach, the monoclonal antibody FE8 or its derivatives may also be combined with other, established forms of treatment, e.g. viral enzyme inhibitors of viral enzymes used during highly active antiretroviral therapy (HAART).

Therefore, according to the invention, it is provided to use a mAb, particularly with the properties shown above, for the manufacture of a therapeutic agent for treating or preventing:

- immune disorders, in particular such ones with the presence of autoantibodies,
- immune responses initiated against self tissue after exposure to substances which may induce the formation of autoantibodies,
- for abrogation/suppression of immune responses initiated against self tissue after exposure to substances which may induce the formation of autoantibodies,
- EBV-related proliferative disorders (in particular B lymphoproliferative syndrome or B-cells tumours occurring under immunosuppressive conditions like HIV-infection or after transplantation),
- infectious diseases where C3dg-coated infectious agents, preferably HIV, are trapped by CR2 expressing cells,
- acute infection with EBV,
- chronic infection with EBV,
- malignant cellular proliferations of CR2-expressing cells with or without involvement of EBV,
- and/or for protection form primary infection with EBV.

The monoclonal antibody FE8 which reacts with SCRs 1 and 2 of CR2 is able to dissociate antigens, particles or pathogens which carry multiple copies of C3dg from CR2. Furthermore the monoclonal antibody FE8, by reacting with SCRs 1 and 2 of CR2, blocks the attachement of EBV and thus inhibits the infection of CR2-expressing cells with this virus.

The invention will now be described by preferred examples:

EXAMPLE 1

FIG. 1 displays that the monoclonal antibody FE8 specifically binds to an epitope located within short consensus repeats 1 to 4 of complement receptor type two (CR2).

To demonstrate the specificity of FE8 for CR2, 100 ng of a recombinant protein comprising the first 4 short consensus repeats of CR2 were adsorbed to individual wells of a 96-well microtitre plate (Maxisorp$^R$, NUNC, Copenhagen, Denmark). This was achieved by incubation in 50 µl of a buffer containing 100 mM sodium hydrogencarbonate (pH 9.6) at 25° C. for 1 hour. The generation of this recombinant protein termed rsCR2.1–4 is in extension described in W. M. Prodinger et al.: "Expression in insect cells of the functional domain of CD21 (complement receptor type two) as a truncated soluble molecule using a baculovirus vector" (Immunopharmacology 38:141–149, 1997).

As a control for rsCR2.1–4, complement factor H (FH), a structurally related protein, was treated identically. After blocking of unspecific binding in each well with 100 µl of blocking buffer (1% bovine serum albumin in saline solution) for 30 min at 25° C., 50 µl of either FE8 or control mAb VIG8 diluted in blocking buffer to 10 µg/ml were added to the wells for two hours at 25° C. VIG8 is directed against FH. All wells were washed thrice with saline solution and 0.05% Tween20$^R$. Bound antibody molecules were detected indirectly by the use of a peroxidase-labeled polyclonal rabbit-antibody against mouse-immunoglobulins (purchased from DAKO, Glostrup, Denmark, and used at the indicated optimal concentration). 50 µl of the conjugate were added to each well for 1 hour at 25° C. After washing as above, 2,2'-azinobis-(3-ethylbenzthiazolinesulfonic acid) was used as substrate at 15 mg per ml of 0.01 M potassium phosphate solution (pH 6.0) containing 0.025% $H_2O_2$. 50 µl of this substrate solution were added to each well for 20 min and the optical density at 405 nm was monitored with an microtitre plate reader. Mean values from two experiments (±SD) are shown.

It is demonstrated that FE8 bound to rsCR2, but not to structurally similar FH, while control VIG8 exhibited the opposite binding pattern, as expected.

EXAMPLE 2

Figure 2:
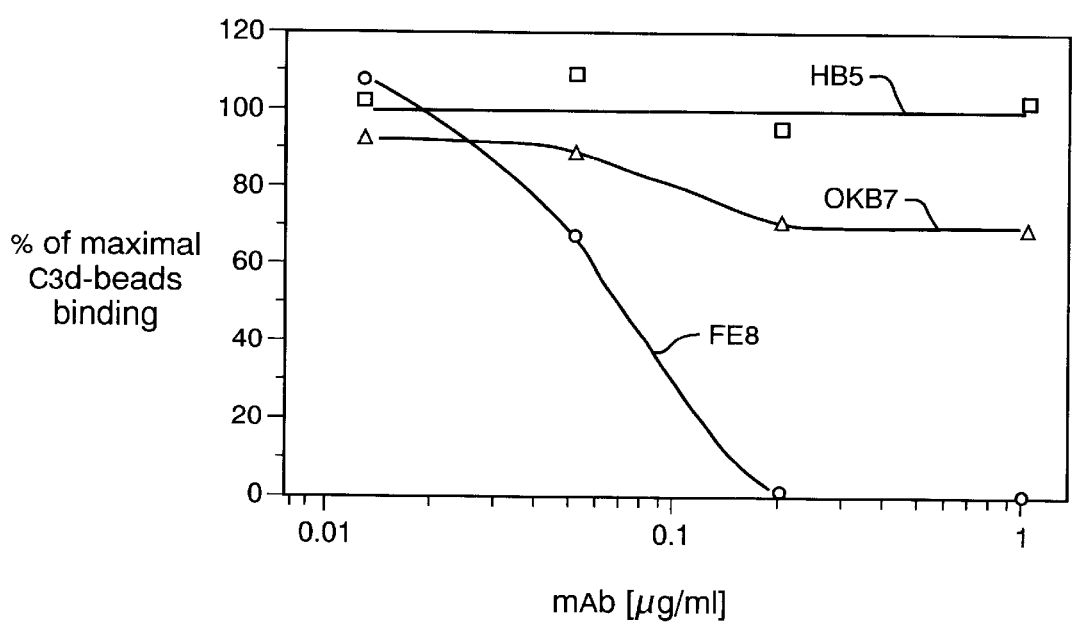
FIG. 2 graphically demonstrates the monoclonal antibody FE8 completely blocks binding of particles carrying polymeric C3dg to CR2.

FIG. 2 displays that the monoclonal antibody FE8 completely blocks binding of particles carrying polymeric C3dg to CR2.

To allow stringent testing for the ability of mAb FE8 to block binding of polymeric C3dg to CR2, fluorescent microbeads carrying multiple copies of C3dg were prepared as essentially described in W. M. Prodinger et al.: "Ligation of the functional domain of complement receptor type 2 (CR2/CD2) is relevant for complex formation in T-cell lines" (J.Immunol. 156:2580–2584, 1996). Raji cells expressing high amounts of CR2 were incubated for 20 min with these beads at 25° C. in the presence of the indicated concentrations of anti-CR2 monoclonal antibodies (i.e., HB5, OKB7, FE8). Then, the cell suspensions were analyzed by flow cytometry on a FACScan (Becton-Dickinson, Hialeah, USA). Raji cells carrying at least one C3dg-microbead exhibited bright green fluorescence and could therefore be distinguished from cells without any C3dg-microbead.

FE8 reduced binding of C3dg-beads at a concentration above 50 ng/ml, and 200 ng/ml were sufficient to abrogate binding of C3dg-microbeads completely. None of the other anti-CR2 mAbs was able to exhibit a similar effect, OKB7 the only antibody known to date to partially interfere with C3dg-binding to CR2, reduced binding of C3dg-microbeads by 30% at most.

EXAMPLE 3

The monoclonal antibody FE8 removes monomeric and polymeric forms of C3dg (which are already attached to CR2) from CR2.

The ability of FE8 to interfere with C3dg which is already bound to CR2 is unique and of major importance to use FE8 to interfere with CR2-mediated enhancement of antibody production or with immobilisation of C3dg-coated antigen by CR2-expressing cells.

Figure 3A:
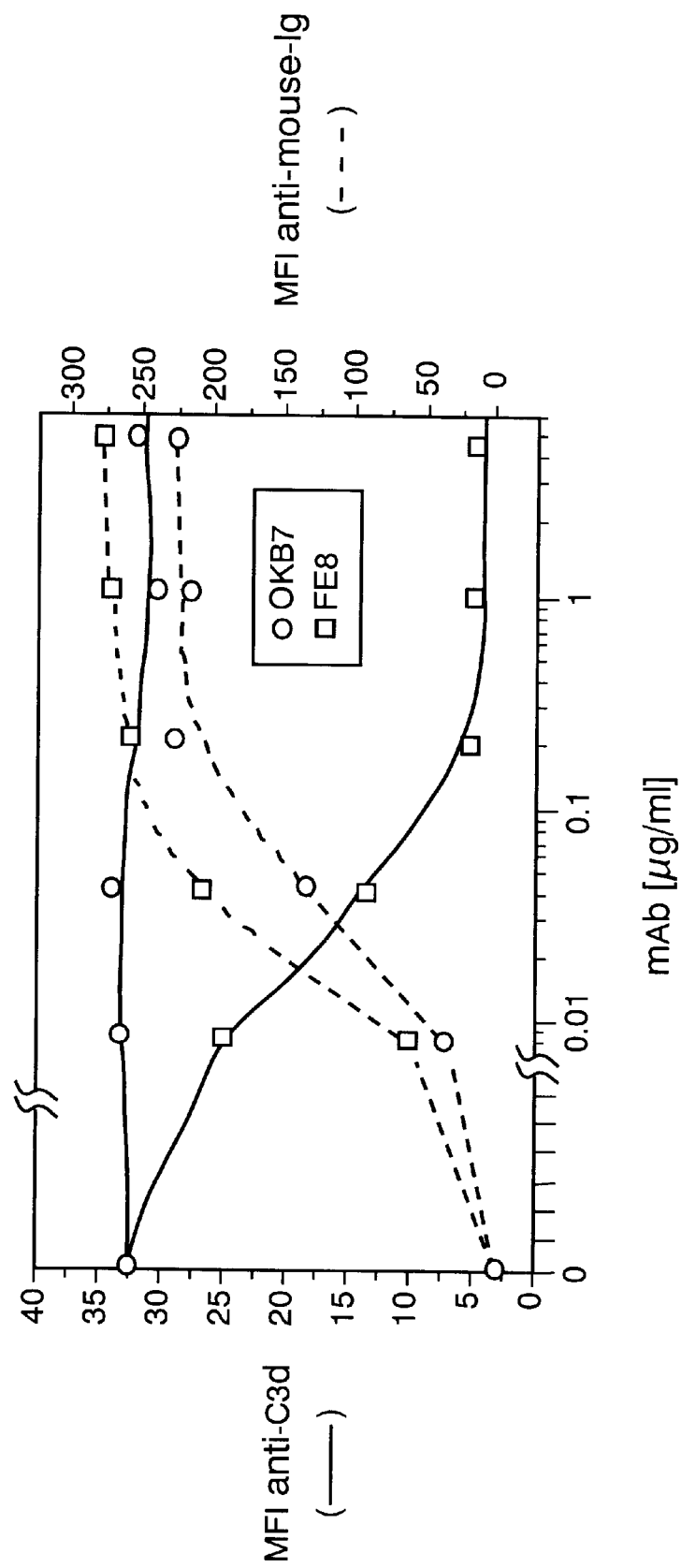
FIG. 3A graphically demonstrates the amount of cell-bound monoclonal antibody and cell-bound C3dg present.

FIG. 3A displays the results of example 3.a, monomeric C3dg was allowed to bind to Raji cells at saturating concentrations for 20 min at 25° C. After washing the cells three times with phosphate-buffered saline solution (PBS) to remove excess C3dg, increasing amounts of monoclonal antibodies FE8 or OKB7 were added to the cells for 10 min at 37° C. After washing the cells again with PBS, the amount of cell-bound monoclonal antibody and of cell-bound C3dg were determined. C3dg (solid lines) was detected by FACS-analysis after staining with FITC-labelled rabbit-anti-C3d antibody, cell-bound monoclonal antibody (dashed lines) was detected by FACS-analysis after staining with phycoerythrine-labelled goat-anti-mouse antibody.

FE8 (squares) is able to displace virtually any cell-bound C3dg at concentrations above 200 ng/ml, because at these concentrations the fluorescence signal drops to background levels. Thus, FE8 and C3dg cannot attach simultaneously to one CR2 molecule. On the other hand, OKB7 and C3dg bind simultaneously to CR2. This means that OKB7 is not able to significantly reduce the amounts of C3dg on the cells, although it is bound to CR2.

In vivo, the low affinity of C3dg to CR2 ($K_a$=27 $\mu$M) helps to discriminate between degradation products of C3 (which continuously form in blood and therefore should not bind to CR2-expressing cells) from particles to which the immune system should respond. These particles contain up to thousands of C3dg molecules and bind to CR2-expressing cells with high avidity.

Figure 3B:
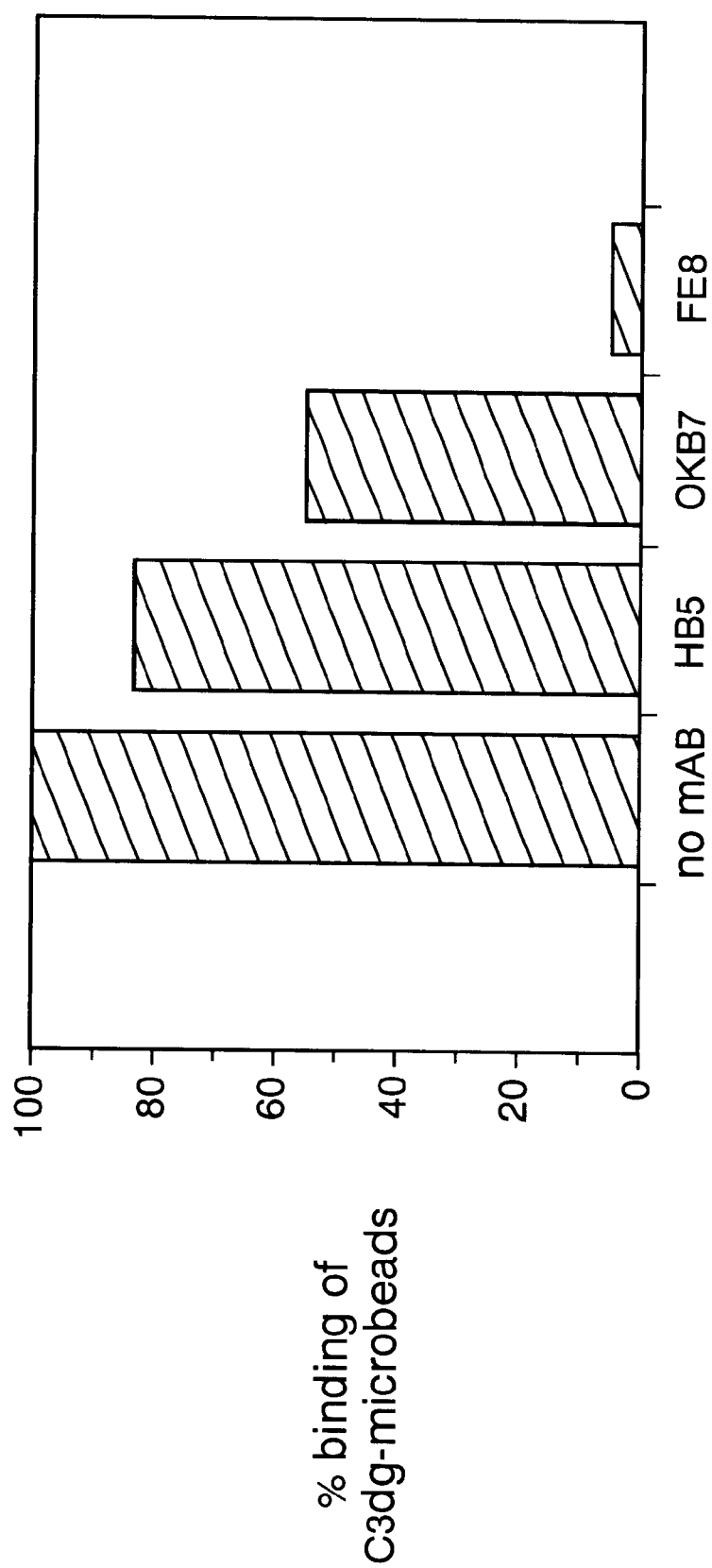
FIG. 3B demonstrates graphically the ability of FE8 to remove bound particles.

FIG. 3B demonstates the unique ability of FE8 to remove such bound particles is illustrated in example 3.b: Raji cells were incubated with fluorescence labelled C3dg-coated agarose-microbeads (see example 2) which mimic opsonized antigens for 20 min, and subsequently monoclonal antibodies against CR2 were added at a concentration of 1 $\mu$g/ml. Binding of the microbeads was measured by fluorescent cell sorting as described above. Only FE8 removed C3dg-coated beads quantitatively.

EXAMPLE 4

Figure 4A:
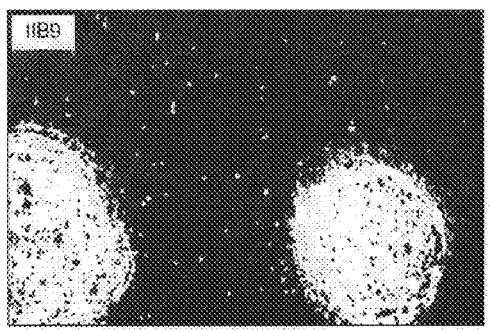
FIG. 4A demonstrates the view as seen by a Axiplan fluorescence microscope when viewing IIB9 under excitation wavelength (fluorescence).
Figure 4B:
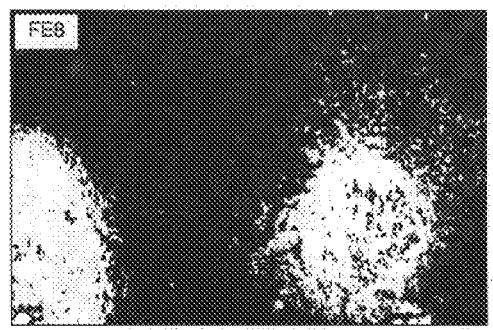
FIG. 4B demonstrates the view as seen by a Axiplan fluorescence microscope when viewing FE8 under excitation wavelength (fluorescence).
Figure 4C:
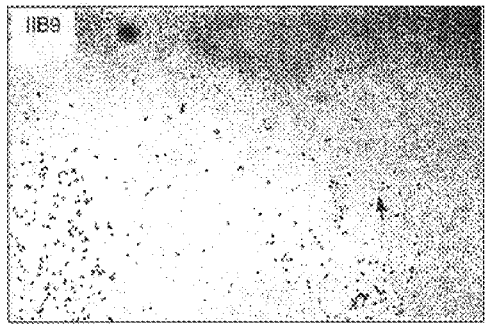
FIG. 4C demonstrates the view as seen by a Axiplan fluorescence microscope when viewing IIB9 under light transmission (no fluorescence).
Figure 4D:
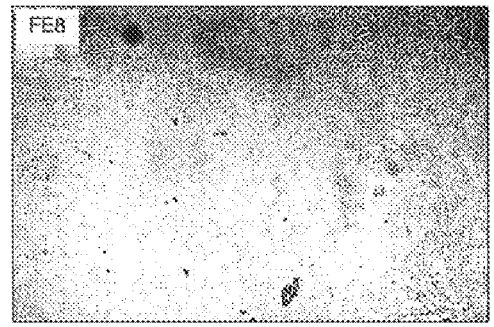
FIG. 4D demonstrates the view as seen by a Axiplan fluorescence microscope when viewing FE8 under light transmission (no fluorescence).

FIGS. 4A–4C displays that the monoclonal antibody FE8 binds to follicular dendritic cells located in the germinal centres of human tonsil follicles and inhibits binding of polymeric C3dg to these cells.

Follicular dendritic cells (FDC) are antigen-retaining cells found in the lymphatic tissue. They express high amounts of CR2, which serves as an anchor to immobilize C3dg-coated antigens on their surface for a long time. FDC are large cells with long cell processes which establish an intimate contact to neighbouring cells. To study the binding of C3dg-coated antigen to FDC in their intact cellular context, snap-frozen microsections (2 $\mu$m thickness) of human tonsils were prepared with a cryo-microtome. The tonsils were obtained from otherwise healthy person undergoing tonsillectomy. The thin sections were fixed onto slides by drying at 25° C. for 2 h. Then, the samples were deep frozen and stored at −80° C. until the experiments were performed. After thawing and drying at 25° C. the sections were incubated with RPMI 1640 cell culture medium (BioWhittaker, Verviers, Belgium) supplemented with 10% fetal calf serum (Kibbuz Beth Haemek, Israel) to minimize unspecific binding. Then, 2 $\mu$g/ml of monoclonal antibody against CR2 were added (FE8 or IIB9, a non-blocking antibody), and incubation was continued for 30 min. Fluorescence labelled C3dg-coated agarose-microbeads (see example 2) were added for 20 min and after washing the samples were fixed with PBS containing 1% paraformaldehyde and 0.1% sodium azide. Bound monoclonal antibody was detected by incubation with phycoerythrine-labelled goat-anti-mouse polyclonal antibodies (DAKO, Glostrup, Denmark).

The slides were viewed in a Axiplan fluorescence microscope (Zeiss, Oberkochen, Germany) either with excitation wavelength (fluorescence) or with light transmission (no fluorescence) and photographed on a 160T ASA film (Ektachrome, Kodak).

As demonstrated in the upper of the FIG. 4, both mAbs react with CR2 and visualize the FDC-network within the germinal centres. The conditions were chosen such that B-lymphocytes, which are also present in these sections and express CR2 exhibit only dim fluorescence due to their relatively lower expression of CR2.

Binding of the C3dg-microbeads on the same sections is illustrated in the lower part of FIG. 4: the beads colocalize with the FDC in the germinal centers in the case of IIB9, suggesting that they mainly bind to FDC via CR2. Again, FE8 is extremly efficient in blocking the attachment of the microbeads to FDC: bound beads are marked by black dots. The arrow points to three beads left unmarked.

EXAMPLE 5

Figure 5:
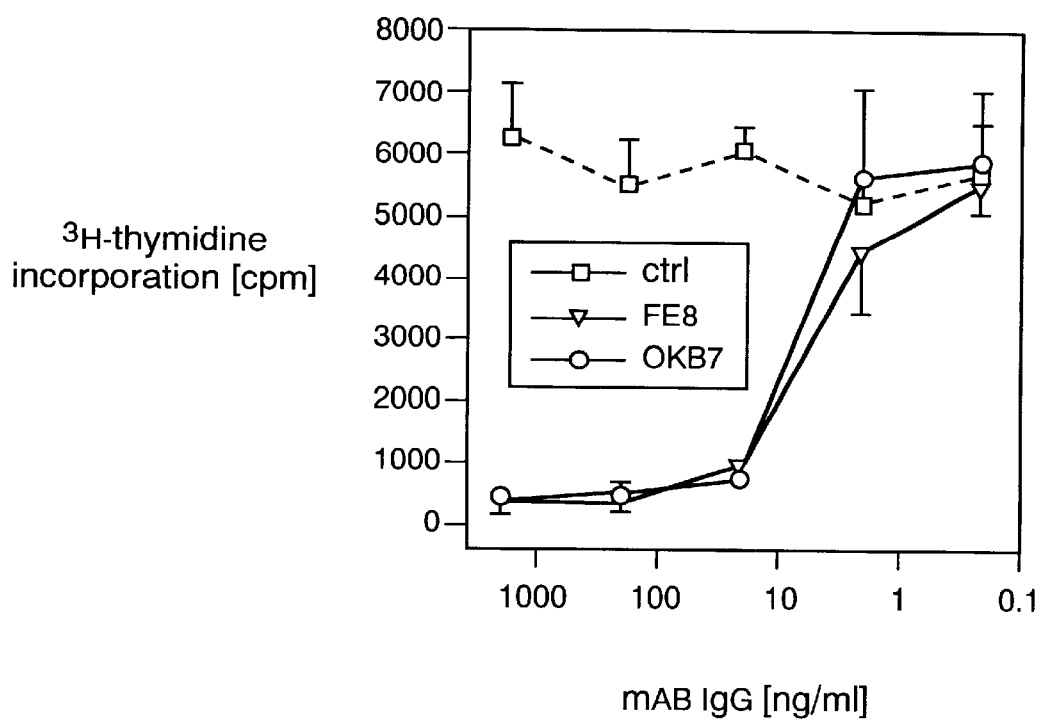
FIG. 5 demonstrates graphically that FE8 reduced $^3$H-thymidine incorporation dose dependently and thus the proliferation of B lymphocytes.

FIG. 5 displays that the monoclonal antibody FE8 inhibits in vitro infection of B-lymphocytes with Epstein-Barr Virus.

Epstein-Barr virus (EBV) is a human herpesvirus which binds directly to CR2 and subsequently infects CR2-expressing cells. The infection provokes that the cell starts to proliferate and multiply. This proliferation of the EBV-infected B-lymphocytes can be quantified by measuring the incorporation of tritiated (i.e. radioactive) thymidine by the cells during DNA-replication.

Here, non-dividing human tonsil B-cells (200,000 in 50 $\mu$l in each well of a 96-well cell culture plate) were incubated with ten-fold dilutions of anti-CR2 monoclonal antibodies FE8 or HB5 (control) were added in 50 $\mu$l of RPMI 1640 medium containing 10% fetal calf serum (see example 4). The cells were incubated at 37° C. with 5% $CO_2$ room atmosphere for 15 min. Then, 150 $\mu$l of EBV-suspension in cell-culture medium were added for further 90 min at 37° C. with 5% $CO_2$ room atmosphere. Spent cell culture supernatant from the cell line B95-8 served as a source of infectious EBV and was used undiluted. After the 90 min, 200 $\mu$l of culture fluid per well were replaced by 200 $\mu$l of RPMI 1640 medium containing 10% fetal calf serum and 0.2 $\mu$g/ml cyclosporin A. Incubation was continued for 10 days. Then 37 kBq of $^3$H-thymidine in 10 $\mu$l of medium were added per well for 24 hours and cell nuclei were harvested onto glass-fiber filters. Incorporated radioactivity was measured by liquid scintillation counting: the glass-fiber filters were given into 1 ml of scintillator fluid (Ultima Gold, Packard) and counted in a Tri-CARB 2200CA beta-counter (Packard). Values are means from triplicate experiments and are shown for one representative donor out three investigated. Bars represent SEM.

The example shows that FE8 reduced $^3$H-thymidine incorporation dose-dependently and thus proliferation of B lymphocytes. Proliferation was due to EBV-infection as B cells without EBV did not proliferate. They had cpm-values between 100 and 200 which were unaltered by the monoclonal antibodies FE8 or HB5. The presence of a control CR2-antibody (HB5) does not reduce multiplication of cells induced by EBV infection.

EXAMPLE 6

Figure 6:
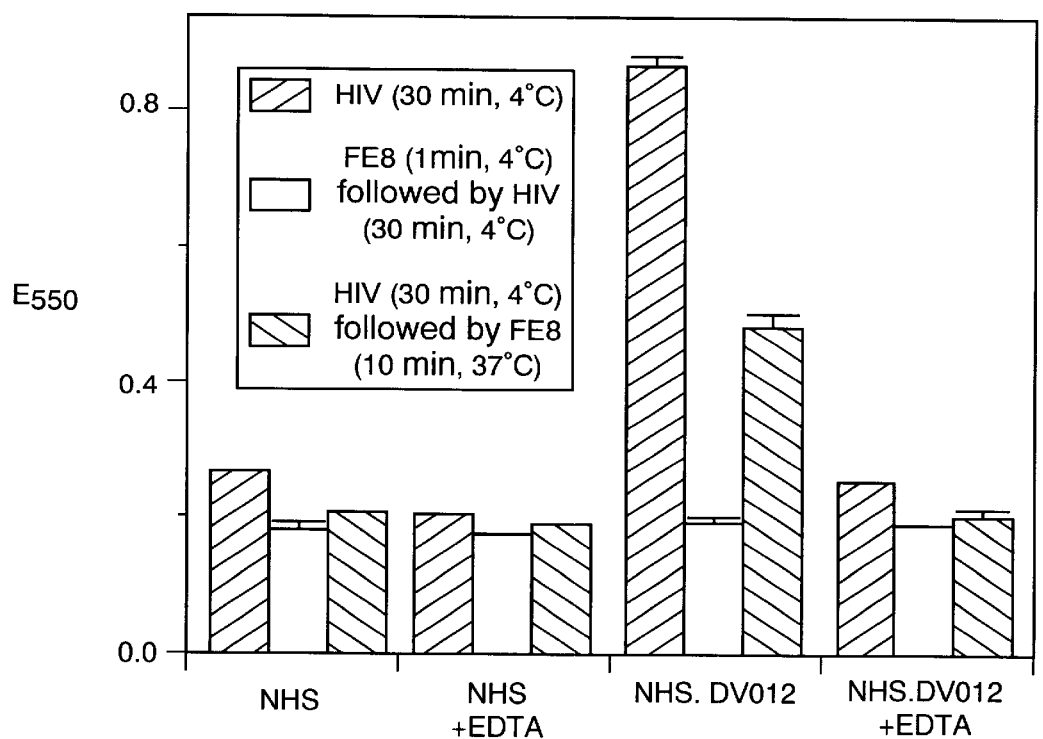
FIG. 6 graphically depicts that the monoclonal antibody FE8 inhibits binding of C3dg-coated human immunodeficiency virus (HIV) to CR2-expressing cells and removes C3dg-coated HIV from these cells.

FIG. 6 dispays that the monoclonal antibody FE8 inhibits binding of C3dg-coated human immunodeficiency virus (HIV) to CR2-expressing cells and removes C3dg-coated HIV from these cells HIV, a human retrovirus which causes the acquired immuno deficiency syndrom (AIDS), is known to attach to target cells like monocytes and T-helper cells via surface molecules which can bind to certain receptors (CD4 and chemokine receptors) of the target cell. HIV in the human body becomes coated with C3dg by complement activation, either by direct binding of the C1q-component of the complement system or with the help of anti-HIV antibodies. It is known that C3dg-coated HIV can bind to CR2-expressing B-lymphocytes and infect these cells in vitro. HIV which is not opsonized cannot bind and infect.

It is furthermore known that CR2-expressing FDC bind C3dg-coated HIV without being infected by the virus, but store infectious HIV for a long period on their surface. As C3dg-coated HIV captured by CR2-expressing cells escapes the immune system as well as an anti-retroviral treatment, a means to flush HIV from CR2-expressing cells will be of importance during HIV therapy.

In this respect, Raji cells were used as a model system for CR2-expressing cells here.

HIV strain IIIB was prepared by expansion of an inoculum in IL-2 (20 U/ml)-activated peripheral blood mononuclear cells of healthy HIV-negative donors. As a measure for virus concentration, 200 ng/ml of viral protein p24 were detected. HIV-IIIB was coated with complement C3-fragments by incubation with normal human serum (diluted 1:10 in RPMI 1640 medium with 10% fetal calf serum as described in examples 4 and 5) and sheep-anti-gp120 polyclonal antibody DV012 (diluted 1:100 in RPMI 1640/10% FCS for 60 min at 37° C. DV012 binds to HIV and is known to lead to C3dg deposition via the classical pathway of complement activation. This pathway strictly depends on the presence of calcium ions and is inhibited by EDTA. As a control, HIV was incubated under the same conditions with normal human serum alone, with normal human serum and 20 mM ethylenediaminetetraacetate (EDTA), or normal human serum and 20 mM EDTA and DV012.

After serum incubation, HIV was pelleted by ultracentrifugation (in a Beckmann L8-M ultracentrifuge at 50,000 g in a SW41Ti rotor for 60 min at 4° C.) and dispensed in 70 $\mu$l RPMI 1640 containing 10% FCS. The virus preparation were added at 1 $\mu$g/ml p24 to 1×10$^6$ Raji cells and incubated for 30 min at 4° C. to allow binding to the cells (shown as black bars in example 6). Experiments were performed in which FE8 was added at 1 $\mu$g/ml (final concentration) to the Raji cells for 1 min at 4° C. before the virus was added (white bars) or for 10 min at 37° C. 30 min after the virus was added (grey bars). Then, the cells were washed three times with phosphate-buffered saline (PBS) to remove unbound virus. To determine the amounts of HIV attached to the cells, the cell pellet was lysed by incubation for 30 min on ice with 200 $\mu$l of ice-cold lysis buffer. Lysis buffer was 50 mM Tris, 300 mM NaCl, 0.5% Triton X-100, 1 mM PMSF, 10 $\mu$g/ml aprotinine adjusted to pH 7.4.

The content of viral protein p24 in this lysate, which is an accepted measure for and proportional to the number of cell-bound virus particles, was determined with an enzyme-linked immunosorbent assay (ELISA) developed by F.Steindl, IAM, Wien.

A mouse mAb against HIV-1 p24 antigen was bound to an ELISA-plate (Greiner, Kremsmünster, Austria) at 200 ng per well. The lysed samples (diluted 1:1 with 1% NP40 in Tris-buffered saline solution (pH 7.4) were added to ca oted wells for 1 h at room temperature. Bound HIV-1 p24 protein was detected with a second biotinylated anti-p24 monoclonal antibody followed by a streptavidin-beta-galactosidase conjugate. The optical density of the colour reaction with resorufin-$\beta$-D-galactopyranoside as substrate (Sigma, St.Louis, Mo.) was measured on an ELISA microplate reader at 550 nm.

As can be seen in example 6, HIV-IIIB bound to Raji via CR2 when incubated with normal human serum and DV012. HIV-IIIB incubated in normal human serum with EDTA did not bind. HIV-IIIB with normal human serum, but without DV012 did not bind, either, which implicates that HIV-IIIB binds to the cells due to coating with C3 fragments, such as C3dg. However, if FE8 was present before C3dg-coated HIV-IIIB was added to Raji cells, no virus particles bound to the cell (white bars). When mAb FE8 was added to the cells which already had large amounts of HIV-IIIB attached on their surface (grey bars), a remarkable reduction of HIV-IIIB was observed.

What is claimed is:

1. A monoclonal antibody (FE8) against human complement receptor type 2 (CR2, CD21) which is able to substantially remove C3-derived fragments already attached to CR2, in particular C3dg from CR2 at temperatures of 25° C. and above.

2. The monoclonal antibody (FE8) according to claim 1 wherein C3-derived fragments bind multiply to CR2 molecules on cells.

3. The monoclonal antibody (FE8) according to claim 2 which is able to dissociate a C3-derived fragment (C3dg) which is bound to the aminoterminal short consensus repeats SCRs 1 and 2 of CR2.

4. The monoclonal antibody according to claim 1 which is able to remove a C3-derived fragment C3dg from CR2 already at a concentration of 0.3$\mu$g/ml and 10$^7$ CR2-positive cells per ml.

5. A monoclonal antibody (FE8) against human complement receptor type 2 (CR2), the antibody recognizing a discontinuous epitope on the aminoterminal short consensus repeats SCRs 1 and 2 of CR2.

6. The monoclonal antibody (FE8) according to claim 5 wherein said antibody (FE8) most intensively reacts with a CR2 epitope located between SCR1 and SCR2 units.

7. The monoclonal antibody (FE8) according to claim 6 wherein said CR2 epitope between SCR1 and SCR2 has the amino acid sequence EYFNKYSS as designated by single letter code.

8. The monoclonal antibody (FE8) according to claim 1 belonging to the mouse immunoglobulin subclass IgG1, K.

9. The monoclonal antibody (FE8) according to claim 1 produced by the hybridoma FE8 deposited at the European Collection of Cell Cultures (ECACC), Salisbury, UK, under accession number 98072910.

10. The monoclonal antibody (FE8) against human complement receptor type 2 (CR2, CD21) according to claim 1, which is able to inhibit completely infection of human CR2 expressing cells with the Epstein-Barr virus.

11. The monoclonal antibody according to claim 10 which is able to block infection of CR2 expressing cells with Epstein-Barr virus already at a concentration of 0.1 $\mu$g/ml and 8×10$^5$-tonsillar B-cells per ml.

12. The monoclonal antibody (FE8) according to claim 1 which is able to block C3-derived fragments normally binding to CR2, such as C3dg, from binding to CR2.

13. A hybridoma wherein said hybridoma produces a monoclonal antibody (FE8) against human complement receptor type 2 (CR2, CD21) which is able to substantially remove C3-derived fragments already attached to CR2, in particular C3dg from CR2 at temperatures of 25° C. and above.

14. The hybridoma according to claim 13, said hybridoma having accession number 98072910 at the European Collection of Cell Cultures (ECACC), Salisbury, UK.

15. A method for the manufacture of a therapeutic agent for treating immune disorders comprising:

identifying immune disorders, in particular such ones with the presence of autoantibodies, immune responses initiated against self tissue after exposure to substances which may induce the formation of autoantibodies wherein the immune disorders identified are selected from the group consisting of disorders caused by Epstein-Barr virus and HIV; and, producing a monoclonal antibody against human complement receptor type 2 (CR2, CD21) and in particular against short consensus repeats SCR1 and SCR2 which treats the identified immune disorder.

16. The method according to claim 15 wherein a therapeutic agent for treating HIV infections is manufactured.

17. The method according to claim 15 wherein the monoclonal antibody is a monoclonal antibody (FE8) against human complement receptor type 2 (CR2, CD21) which is able to substantially remove C3-derived fragments already attached to CR2, in particular C3dg from CR2 at temperatures of 25° C. and above.

18. The method as set forth in claim 17 wherein the monoclonal antibody is used as a therapeutic or diagnostic agent.

19. A pharmaceutical composition comprising an effective amount of a monoclonal antibody (FE8) against human complement receptor type 2 (CR2, CD21) which is able to substantially remove C3-derived fragments already attached to CR2, in particular C3dg from CR2 at temperatures of 25° C. and above optionally in combination with a pharmaceutically acceptable carrier and/or one or more drugs used to treat pathological conditions.

20. A method for preparing a pharmaceutical composition comprising the steps of:

providing an effective amount of monoclonal antibody (FE8) against human complement receptor type 2 (CR2, CD21) which is able to substantially remove C3-derived fragments already attached to CR2, in particular C3dg from CR2 at temperatures of 25° C. and above in a form suitable for a pharmaceutical composition; and, combining said monoclonal antibody with a pharmaceutically acceptable carrier.

21. A method for preparing monoclonal antibodies comprising the steps of:

a) preparing a CR2 molecule comprising at least short consensus repeats SCRs 1 to 2 of CR2, and preferably SCRs 1 to 4 of CR2;

b) immunizing rodents, in particular mice, with a solution thereof, which is preferably made in PBS at pH 8.5;

c) fusing spleen cells from said rodents with a myeloma cell line and culturing said fused cells with HAT medium;

d) coating carrier particles with a C3-derived fragment binding to CR2, in particular with C3d;

e) labeling said carrier particles with tracers, preferably fluoresceinisothiocyanate (FITC);

f) testing hybridoma clones to determine which produce monoclonal antibodies with florescence activated cell sorting; and, g) selecting hybridoma clones which produce monoclonal antibodies for their cell culture supernatants for the potential to remove from CR2 said coated carrier particles after they had bound to CR2-expressing cells.

22. The method of claim 21 wherein the carrier particles are agarose beads having a diameter of 1 µm and lower.

23. The method of claim 21 wherein coating of the carrier particles is effected by sequential incubation with human serum and trypsin.

* * * * *